United States Patent
Mogi et al.

(10) Patent No.: US 6,362,203 B1
(45) Date of Patent: Mar. 26, 2002

(54) 4-HYDROXY-4-PHENYLPIPERIDINE DERIVATIVES AND PHARMACEUTICALS CONTAINING THE SAME

(75) Inventors: Kinichi Mogi; Yoshihiko Kanamaru; Noriyuki Kawamoto, all of Narita; Teruo Komoto, Chiba; Norimitsu Umehara, Tokorozawa; Susumu Sato, Narita; Tetsuo Oka, Hiratsuka, all of (JP)

(73) Assignee: SSP Co., LTD, Tokyo (JP)

( * ) Notice: Subject to any disclaimer, the term of this patent is extended or adjusted under 35 U.S.C. 154(b) by 0 days.

(21) Appl. No.: 09/698,041

(22) Filed: Oct. 30, 2000

(30) Foreign Application Priority Data

Nov. 8, 1999 (JP) ............................................ 11-316881

(51) Int. Cl.⁷ ...................... C07D 211/52; A61K 31/445
(52) U.S. Cl. ........................ 514/327; 546/192; 546/217; 514/317
(58) Field of Search ................................ 546/192, 217; 514/327, 317

(56) References Cited

FOREIGN PATENT DOCUMENTS

| JP | 47-000173 | 1/1972 | |
|---|---|---|---|
| WO | WO 97/09973 | 3/1997 | |
| WO | WO 98/54196 | * 12/1998 | .................. 514/327 |

OTHER PUBLICATIONS

M. Williams, et al., Journal of Medicinal Chemistry, vol. 42, No. 9, pp. 1481–1500, "Emerging Molecular Approaches to Pain Therapy," May 6, 1999.
C. Stein, et al., The Journal of Pharmacology and Experimental Therapeutics, vol. 248, No. 3, pp. 1269–1275, "Peripheral Opioid Receptors Mediating Antinociception in Inflammation. Evidence for Involvement of MU, Delta, and Kappa Receptors," 1989.
P.L Bigliardi, et al., The Journal of Investigative Dermatology, vol. 111, No. 2, pp. 297–301, "Expression of μ–Opiate Receptor in Human Epidermis and Keratinocytes," Aug. 1998.
N. Nozaki, et al., Anesthesiology, vol. 90, No. 1, pp. 225–234, "Characterization of the Antihyperalgesic Action of a Novel Peripheral MU–Opioid Receptor Agonist–Loperamide," Jan. 1999.
D.L. Dehaven–Hudkins, et al., vol. 289, No. 1, pp. 494–502, "Loperamide (ADL 2–1294), an Opioid Antihyperalgesic Agent with Peripheral Selectivity," 1999.
F.H. Epstein, Mechanisms of Disease, vol. 332, No. 25, pp. 1685–1690, "The Control of Pain in Peripheral Tissue by Opioids," Jun. 22, 1995.

* cited by examiner

Primary Examiner—Zinna Northington Davis
(74) Attorney, Agent, or Firm—Oblon, Spivak, McClelland, Maier & Neustadt, P.C.

(57) ABSTRACT

Described is a 4-hydroxy-4-phenylpiperidine derivative represented by the following formula (1):

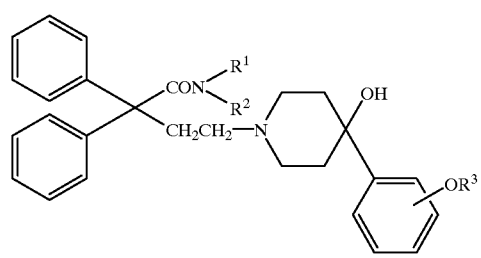

(1)

[wherein, $R^1$ and $R^2$ are the same or different and each independently represents a hydrogen atom, a lower alkyl, or the like, $R^3$ represents a hydrogen atom or a group $-(CR^4R^5)_n-Y$ (in which, $R^4$ and $R^5$ each represents a hydrogen atom or a lower alkyl group, Y represents a group $-COOR^6$, $-CONR^7R^8$, $-OR^9$ or $-OCOR^{10}$ (in which $R^6$, $R^9$ and $R^{10}$ each independently represents a hydrogen atom, a lower alkyl group, or the like, $R^7$ and $R^8$ are the same or different and each independently represents a hydrogen atom, a lower alkyl group, or the like), and n stands for 1 to 6)], or salt thereof.

The compound exhibits excellent peripheral analgesic action.

6 Claims, No Drawings

4-HYDROXY-4-PHENYLPIPERIDINE DERIVATIVES AND PHARMACEUTICALS CONTAINING THE SAME

TECHNICAL FIELD

The present invention relates to 4-hydroxy-4-phenylpiperidine derivatives excellent in peripheral analgesic action or salts thereof; and pharmaceuticals containing the same.

BACKGROUND ART

As an analgesic, known are central opioid analgesics typified by morphine, non-steroidal anti-inflammatory drugs (NSAIDS) typified by indomethacin and local anesthetics typified by lidocaine [The Journal of Medicinal Chemistry, 42(9), 1481(1999) and cited references described therein].

Morphine however cannot be used freely because of its undesirable central side effects. In addition, there are pains against which neither non-steroidal anti-inflammatory drugs nor local anesthetics have sufficient analgesic effects. There is accordingly a demand for the development of a medicament which is safer and has higher analgesic effects than them.

In recent years, existence of a μ-receptor at the periphery has been revealed and analgesic action via this receptor has come to be elucidated [The Journal of Pharmacology and Experimental Therapeutics, 248(3), 1269(1989); The Journal of Investigative Dermatology, 111, 297(1988); and Drug Therapy, 323, 1685(1995)].

In Japanese Patent Application Laid-Open No. Sho 47-173, described are diarylpiperidinobutylamide compounds and among them, loperamide developed as a stegnotic is under development as a peripheral analgesic [Anesthesiology, 90, 225(1999); The Journal of Pharmacology and Experimental Therapeutics, 289, 494(1999)].

The peripheral analgesic action of loperamide is however not always satisfactory.

An object of the present invention is therefore to provide a compound excellent in peripheral analgesic action.

DISCLOSURE OF THE INVENTION

With the foregoing in view, the present inventors have carried out an extensive investigation to obtain a compound having excellent peripheral analgesic action. As a result, it has been found that a 4-hydroxy-4-phenylpiperidine derivative represented by the below-described formula (1) is markedly superior to the above-described loperamide in peripheral analgesic action and is therefore useful as a medicament, leading to the completion of the present invention.

In one aspect of the present invention, there is thus provided a 4-hydroxy-4-phenylpiperidine derivative represented by the following formula (1):

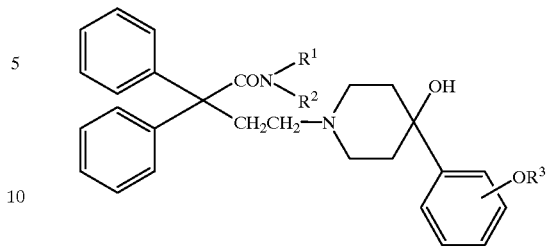

[wherein, $R^1$ and $R^2$ are the same or different and each independently represents a hydrogen atom, a lower alkyl group or a cycloalkyl group, or $R^1$ and $R^2$ may form a heterocyclic group together with the adjacent nitrogen atom, $R^3$ represents a hydrogen atom or a group —$(CR^4R^5)_n$—Y (in which, $R^4$ and $R^5$ each represents a hydrogen atom or a lower alkyl group, Y represents a group —$COOR^6$, —$CONR^7R^8$, —$OR^9$ or —$OCOR^{10}$ (in which $R^6$, $R^9$ and $R^{10}$ each independently represents a hydrogen atom, a lower alkyl group or a cycloalkyl group, $R^7$ and $R^8$ are the same or different and each independently represents a hydrogen atom, a lower alkyl group or a cycloalkyl group or $R^7$ and $R^8$ may form a heterocyclic ring together with the adjacent nitrogen atom), and n stands for 1 to 6)], or salt thereof; and a medicament containing it or its salt as an effective ingredient.

In another aspect of the present invention, there is also provided a pharmaceutical composition containing the above-described 4-hydroxy-4-phenylpiperidine derivative or salt thereof and a pharmaceutically acceptable carrier.

In a further aspect of the present invention, there is also provided use of the above-described 4-hydroxy-4-phenylpiperidine derivative or salt thereof as a medicament.

In a still further aspect of the present invention, there is also provided a paint treating method, which comprises administering the above-described 4-hydroxy-4-phenylpiperidine derivative or salt thereof.

BEST MODE FOR CARRYING OUT THE INVENTION

Examples of the lower alkyl group as $R^1$ or $R^2$ in the formula (1) of the invention compound (1) include linear or branched $C_{1-6}$ alkyl groups, more specifically, methyl, ethyl, n-propyl, i-propyl, n-butyl, i-butyl, sec-butyl, tert-butyl, n-pentyl and n-hexyl groups. As the cycloalkyl group, $C_{3-8}$ ones are preferred. Specific examples include cyclopropyl, cyclobutyl, cyclopentyl, cyclohexyl, cycloheptyl and cyclooctyl groups. Among them, hydrogen atom and $C_{1-6}$ alkyl groups are particularly preferred as each of $R^1$ and $R^2$.

The number of the member of the heterocyclic ring formed by $R^1$ and $R^2$ together with the adjacent nitrogen atom is preferably 5 to 8. Examples of such a ring include pyrrolidine, piperidine, piperazine and morpholine rings, of which the pyrrolidine ring is particularly preferred.

Examples of the lower alkyl group as $R^4$ or $R^5$ include linear or branched $C_{1-6}$ alkyl groups, more specifically, methyl, ethyl, n-propyl, i-propyl, n-butyl, i-butyl, sec-butyl, tert-butyl, n-pentyl and n-hexyl groups. As $R^4$ or $R^5$, a hydrogen atom is preferred.

Examples of the lower alkyl group as $R^6$, $R^7$, $R^8$, $R^9$ or $R^{10}$ include linear or branched $C_{1-6}$ alkyl groups, more specifically, methyl, ethyl, n-propyl, i-propyl, n-butyl, i-butyl, sec-butyl, tert-butyl, n-pentyl and n-hexyl groups. As the cycloalkyl group, $C_{3-8}$ ones are preferred. Specific examples include cyclopropyl, cyclobutyl, cyclopentyl, cyclohexyl, cycloheptyl and cyclooctyl groups.

The number of the member of the heterocyclic ring formed by $R^7$ and $R^8$ together with the adjacent nitrogen atom is 5 to 8. Examples of such a ring include pyrrolidine, piperidine, piperazine and morpholine rings. As $R^6$, hydrogen atom and $C_{1-6}$ alkyl groups (particularly, ethyl) are preferred, while as $R^9$, hydrogen atom and $C_{1-6}$ alkyl groups (particularly, methyl) are preferred. As $R^{10}$, $C_{1-6}$ alkyl groups, particularly, methyl group is preferred. n stands for 1 to 6, of which 1 to 3 is preferred.

No particular limitation is imposed on the salt of the invention compound (1) insofar as it is a pharmaceutically acceptable salt thereof. Examples include addition salts of an inorganic acid such as hydrochloric acid, sulfuric acid, hydrobromic acid or phosphoric acid and addition salts of an organic acid such as formic acid, acetic acid, fumaric acid, maleic acid or tartaric acid. The invention compounds also embrace solvates such as hydrates.

Each of the 4-hydroxy-4-phenylpiperidine derivatives and salts thereof according to the present invention can be prepared, for example, by any one of the following (Process A) to (Process C).

(Process A)

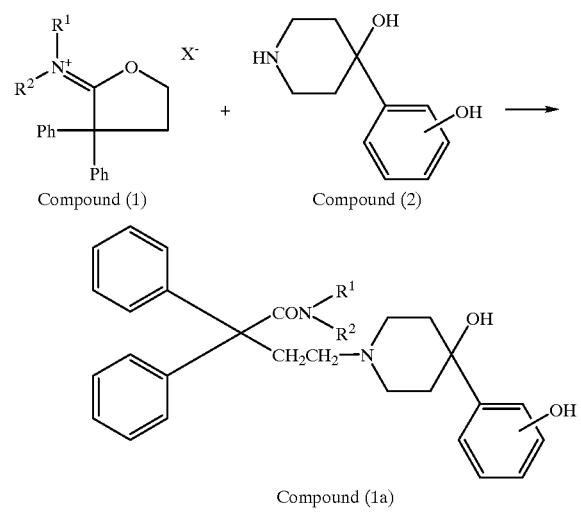

Compound (1a)

[wherein, X represents a halogen atom, and $R^1$ and $R^2$ have the same meanings as described above].

Described specifically, Invention compound (1a) is available by reacting Compound (1) with Compound (2). This reaction is usually conducted in the presence of 2 to 5 equivalents, preferably 3 equivalents of a base at 40 to 100° C., preferably 50 to 60° C. for 1 to 3 hours. This reaction can be conducted in an anhydrous solvent such as benzene, toluene, tetrahydrofuran or dimethylformamide. Examples of the base include inorganic bases such as sodium carbonate and sodium hydroxide and organic bases such as triethylamine.

Each of Compound (1) and Compound (2) can be synthesized in a known manner.

(Process B)

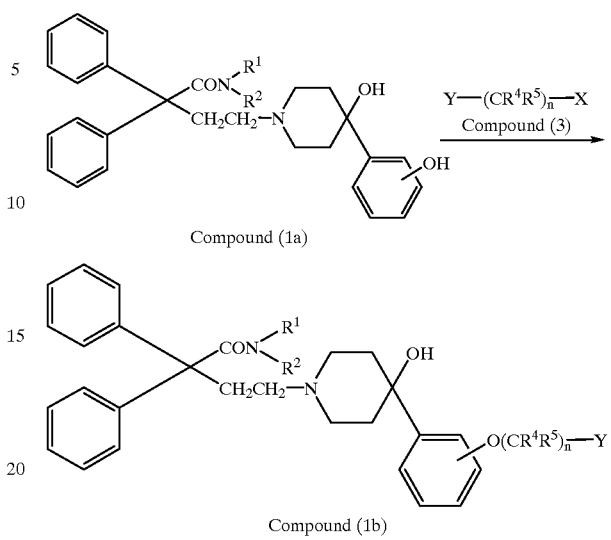

[wherein, n stands for 1 to 6, and $R^1$, $R^2$, $R^4$, $R^5$, X and Y have the same meanings as described above].

Described specifically, Invention compound (1b) is available by reacting Compound (1a) with Compound (3). This reaction is usually conducted in the presence of 1 to 3 equivalents, preferably 1 to 1.5 equivalents of a base at 20 to 100° C., preferably 20 to 60° C. for 2 to 36 hours. This reaction can be conducted in an anhydrous solvent such as acetone, tetrahydrofuran, dimethylformamide or dimethylsulfoxide. Examples of the base include inorganic bases such as sodium carbonate, sodium hydroxide and sodium hydride and organic bases such as triethylamine. The base may be added together with potassium iodide.

Compound (3) is commercially available as a reagent easily or can be synthesized in a known manner.

(Process C)

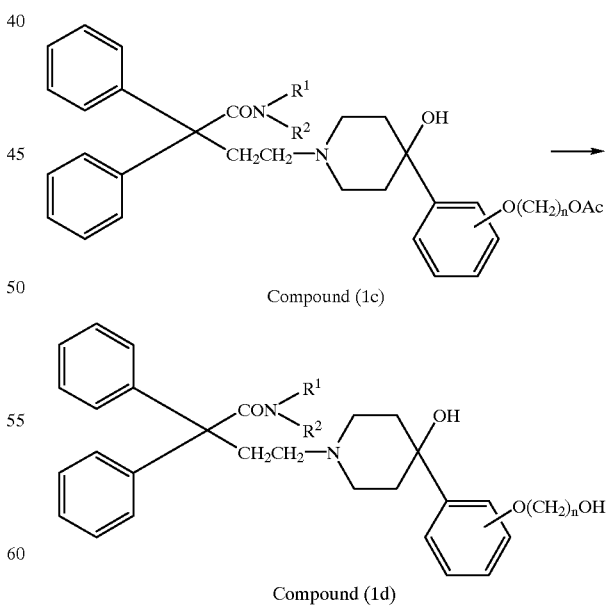

[wherein, $R^1$, $R^2$ and n have the same meanings as described above].

Described specifically, Invention compound (1d) is available by hydrolyzing Compound (1c) (Compound (1b)

wherein $R^4$, $R^5$=H, and Y=OAc) which has been synthesized by Process (B). This reaction is usually conducted in the presence of 1 to 3 equivalents, preferably 1 to 1.5 equivalents of a base at 20 to 40° C., preferably 20 to 25° C. for 1 to 5 hours. This reaction can be conducted in a water miscible solvent such as methanol, ethanol, dioxane or tetrahydrofuran. Examples of the base include inorganic bases such as sodium hydroxide, potassium hydroxide and sodium carbonate.

A salt of Invention Compound (1) is available, for example, by reacting Compound (1) with 1 to 2 equivalents, preferably 1 to 1.2 equivalents of an acid in an anhydrous solvent at 0 to 30° C. for 0.1 to 0.5 hour. Preferred examples of the solvent include anhydrous ether, anhydrous tetrahydrofuran, anhydrous chloroform, anhydrous dioxane and anhydrous acetone. As the acid, the above-exemplified ones can be employed.

Invention compound (1) or salt thereof thus obtained can be purified by using ordinary methods such as column chromatography and recrystallization in combination.

Invention compound (I) or salt thereof exhibits excellent $\mu$-opioid agonist action as described later in Tests and is therefore useful as a peripheral analgesic for animals including human being. The peripheral analgesic of the present invention can be used for the suppression or prevention of pain in various diseases (ex. various inflammatory diseases including arthritis and cancer), after operation, or in injury, fracture or burn.

Invention compound (1) or salt thereof, together with a pharmaceutically acceptable carrier, can be formed into a pharmaceutical composition of various dosage forms in a conventional manner. No particular limitation is imposed on the administration form and it can be selected as needed depending on the treating purpose. For example, administration can be conducted through any one of an orally dosable agent, injection, suppository, ointment and plaster. Such administration forms can each be manufactured in a manner known to those skilled in the art.

An orally dosable solid preparation such as tablet, coated tablet, granule, powder or capsule can be prepared by adding, to Invention compound (1), an excipient and if necessary, binder, disintegrator, lubricant, colorant, taste corrigent and smell corrigent and then treating the resulting mixture in a conventional manner.

An orally administrable liquid preparation such as a liquid preparation for internal use, syrup or elixir can be prepared by adding, to Invention compound (1), a taste corrigent, buffer, stabilizer or smell corrigent and then treating the resulting mixture in a conventional manner.

An injection such as subcutaneous, intramuscular or intravenous injection can be prepared by adding, to Invention compound (1), a pH regulator, buffer, stabilizer, isotonizing agent or local anesthetic agent and then treating the resulting mixture in a conventional manner.

A suppository can be prepared by adding, to Invention compound (1), a pharmaceutical carrier known to those skilled in the art, for example, polyethylene glycol, lanolin, cacao butter or fatty acid triglyceride and if necessary, a surfactant and then treating the resulting mixture in a conventional manner.

An ointment can be prepared by incorporating an ordinarily employed base material, stabilizer, humectant, preservative or the like as needed, and mixing them in a conventional manner.

A plaster may be prepared by applying the above-described ointment, or cream, gel, paste or the like, each made in a respective conventional manner, to an ordinarily employed backing material in a conventional manner.

The amount of Invention compound (1) to be incorporated in each of the above-described dosage forms differs depending on the conditions of the patient to be administered or the dosage form. In general, it is desired to incorporate it in an amount of about 0.25 to 100 mg for an orally dosable preparation, about 0.05 to 20 mg for an injection and about 0.1 to 50 mg for a suppository. The daily dose of the medicament in the above-described dosage form cannot be determined in a wholesale manner, because it differs with the symptom, body weight, age, sex, etc. of the patient. Usually, the daily dose may be about 0.005 to 2 mg/kg, preferably about 0.01 to 0.1 mg/kg per adult. It is desired to conduct administration once or in 2 to 4 portions a day.

EXAMPLES

The present invention will hereinafter be described in detail by examples. It should however be borne in mind that the present invention is not limited to or by them.

Referential Example 1

4-Bromo-2,2-diphenylbutyric acid 23 g (72 mmol) was suspended in 150 mL of chloroform. At room temperature, 20 mL (270 mmol) of thionyl chloride was added dropwise to the resulting suspension. After addition of 0.2 mL of dimethylformamide, the resulting mixture was heated under reflux for 4 hours. After completion of the reaction, the solvent was concentrated under reduced pressure, whereby 23 g (yield: 94.7%) of 4-bromo-2,2-diphenylbutyric chloride was obtained.

In 100 mL of water were suspended 8 g (90 mmol) of a 50% aqueous solution of dimethylamine and 18 g (170 mmol) of sodium carbonate, followed by cooling to 0 to 5° C. A solution obtained by dissolving 23 g (68 mmol) of the 4-bromo-2,2-diphenylbutyric chloride mentioned above in 100 mL of toluene was then added dropwise. After stirring for 2 hours, the water layer taken out from the reaction mixture was washed with toluene. The resulting water layer was extracted with chloroform. The extract was washed with water and then dried. The residue obtained by concentrating the solvent under reduced pressure was crystallized from methyl isobutyl ketone, whereby 11 g (yield: 46.8%) of dimethyl(tetrahydro-3,3-diphenyl-2-furylidene)ammonium bromide was obtained.

$^1$H-NMR (CDCl$_3$) $\delta$ (ppm): 7.40–7.60(10H,m), 4.85(2H,t), 3.83(3H,s), 3.47(2H,t), 2.96(3H,s).

Referential Example 2

To 30 mL of anhydrous tetrahydrofuran was added 940 mg (39 mmol) of magnesium powder. The one-fifth of a solution obtained by dissolving 10 g (38 mmol) of 2-benzyloxybromobenzene in 30 mL of anhydrous tetrahydrofuran was added. To the resulting mixture were added 0.1 mL of 1,2-dibromoethane and a small amount of iodine, followed by heating to 60 to 70° C. When the reaction started, the remaining portion of the anhydrous tetrahydrofuran solution of 2-benzyloxybromobenzene was added dropwise and the mixture was heated to reflux for further 30 minutes. In the resulting anhydrous tetrahydrofuran solution of Grignard reagent, 7 g (37 mmol) of 1-benzyl-4-piperidone dissolved in 30 mL of anhydrous tetrahydrofuran was added dropwise at room temperature. After heating to reflux for 30 minutes, 10 mL of a saturated aqueous solution of ammonium chloride was added dropwise and the solvent was concentrated under reduced pressure. Water was added to the residue and the mixture was extracted with ether, followed by washing with water and drying. The residue obtained by concentrating the solvent under reduced pressure was purified by chromatography on a silica gel column, whereby 12 g (yield: 87.0%) of 1-benzyl-4-(2-benzyloxyphenyl)-4-piperidinol was obtained.

$^1$H-NMR (CDCl$_3$) δ (ppm): 7.20–7.50(12H,m), 6.95–7.00 (2H,m), 5.15(2H,s), 4.01(1H,s), 3.55(2H,s), 2.70–2.80(2H,m), 2.45–2.60(2H,m), 2.10–2.20(2H,m), 2.00–2.10(2H,m).

Referential Example 3

In 100 mL of methanol was dissolved 12 g (32 mmol) of 1-benzyl-4-(2-benzyloxyphenyl)-4-piperidinol. To the resulting solution was added 3 g of 20% palladium hydroxide carbon and the resulting mixture was subjected to catalytic reduction at room temperature for 6 hours under 4 atmospheric pressure. After completion of the reaction, the catalyst was filtered off and the filtrate was concentrated under reduced pressure, whereby 6.7 g (yield: 100%) of 4-(2-hydroxyphenyl)-4-piperidinol was obtained.

$^1$H-NMR (DMSO-d$_6$) δ (ppm): 7.22(1H,dd), 7.05(1H, ddd), 6.70–6.80(2H,m), 4.8(br.), 2.95(2H,ddd), 2.70–2.80 (2H,m), 2.03(2H,ddd), 1.60–1.70(2H,m).

Referential Example 4

In a similar manner to Referential Example 1 except for the use of diethylamine instead of a 50% aqueous solution of dimethylamine, diethyl(tetrahydro-3,3-diphenyl-2-furylidene)ammonium bromide was obtained (yield: 51.0%).

$^1$H-NMR (CDCl$_3$) δ (ppm): 7.20–7.60(10H,m), 4.97(2H,t), 4.07(2H,q), 3.52(2H,t), 3.42(2H,q), 1.50(3H,t), 0.60(3H,t).

Referential Example 5

In a similar manner to Referential Example 1 except for the use of pyrrolidine instead of a 50% aqueous solution of dimethylamine, (tetrahydro-3,3-diphenyl-2-furylidene) pyrrolidinium bromide was obtained (yield: 53.6%).

$^1$H-NMR (CDCl$_3$) δ (ppm): 7.25–7.70(10H,m), 4.88(2H,t), 4.37(2H,t), 3.50(2H,t), 2.88(2H,t), 1.80–2.30 (4H,m).

Referential Example 6

In a mixed solvent of 60 mL of dioxane and 50 mL of water were dissolved 3.16 g (10 mmol) of 4-bromo-2,2-diphenylbutylonitrile and 1.93 g (10 mmol) of 4-(2-hydroxyphenyl)-4-piperidinol. To the resulting solution was added 2.76 g (20 mmol) of sodium carbonate, followed by heating under reflux for 12 hours. The reaction mixture was distilled under reduced pressure to remove the solvent. The residue thus obtained was dissolved in ethyl acetate, followed by washing with water and drying. The residue obtained by concentrating the solvent under reduced pressure was recrystallized from a mixed solvent of chloroform, ether and methanol, whereby 1.96 g (yield: 47.6%) of 4-(4-hydroxy-4-(2-hydroxyphenyl)piperidino)-2,2-diphenylbutylonitrile was obtained.

$^1$H-NMR (CDCl$_3$) δ (ppm): 9.69(1H,br), 7.20–7.50(11H,m), 7.00–7.15(1H,m), 6.70–6.80(2H,m), 5.47(1H,br), 2.55–2.75(4H,m), 2.20–2.40(4H,m), 2.10–2.20 (2H,m), 1.62(2H,d).

Referential Example 7

Reaction was conducted as in referential Example 6, whereby 4-(4-hydroxy-4-((2-acetoxyethoxy)phenyl) piperidino)-2,2-diphenylbutylonitrile was obtained (yield: 99.0%).

$^1$H-NMR (CDCl$_3$) δ (ppm): 7.20–7.50(12H,m), 6.98(1H,t), 6.88(1H,d), 4.48(2H,t), 4.25(2H,t), 4.04(1H,s), 2.50–2.80(8H,m), 2.09(3H,s), 2.00–2.15(4H,m).

Referential Example 8

In 5 mL of chloroform was suspended 5.00 g (15.7 mmol) of 4-bromo-2,2-diphenylbutyric acid. Thionyl chloride (10 mL) was then added dropwise at room temperature. To the resulting mixture was added 0.1 mL of dimethylformamide, followed by heating under reflux for 5 hours. After completion of the reaction, the solvent was concentrated under reduced pressure, whereby 4-bromo-2,2-diphenylbutyric chloride was obtained. While stirring under ice cooling, 50 mL of cold methanol was added. The temperature was allowed to rise back to room temperature, and then stirring was conducted for 30 minutes. The residue obtained by concentrating the solvent under reduced pressure was purified by chromatography on a silica gel column, whereby 5.00 g (yield: 95.7%) of methyl 4-bromo-2,2-diphenylbutyrate was obtained.

$^1$H-NMR (CDCl$_3$) δ ppm: 7.10–7.50(10H,m), 3.71(3H,s), 2.80–3.30(4H,m).

Referential Example 9

In 50 mL of anhydrous dimethylformamide were dissolved 2.24 g (6.7 mmol) of methyl 4-bromo-2,2-diphenylbutyrate and 1.30 g (6.7 mmol) of 4-(2-hydroxyphenyl)-4-piperidinol. To the resulting solution was added 1.07 g (10 mmol) of sodium carbonate, followed by stirring under heating at 50° C. for 35 hours. The residue obtained by distilling off the solvent under reduced pressure was dissolved in ethyl acetate, followed by washing with water and drying. The residue obtained by concentrating the solvent under reduced pressure was purified by chromatography on a silica gel column, whereby 870 mg (yield: 29.2%) of methyl 4-(4-hydroxy-4-(2-hydroxyphenyl) piperidino)-2,2-diphenylbutyrate was obtained.

$^1$H-NMR (CDCl$_3$) δ (ppm): 7.20–7.35(10H,m), 7.05–7.18 (2H,m), 6.80–6.87(2H,m), 3.69(3H,s), 2.75–2.85(2H,m), 2.60–2.70(2H,m), 2.30–2.50(2H,m), 3.05–2.30(4H,m), 1.98 (2H,d).

Referential Example 10

Reaction was conducted as in referential Example 9, whereby methyl 4-(4-hydroxy-4-(2-(2-acetoxyethoxy) phenyl)piperidino)-2,2-diphenylbutyrate was obtained (yield: 77.3%).

$^1$H-NMR (CDCl$_3$) δ (ppm): 6.80–7.40(14H,m), 4.36–4.60 (2H,m), 4.10–4.35(2H,m), 4.05(1H,s), 3.69(3H,s), 1.80–2.90(12H,m), 2.09(3H,s).

Referential Example 11

In a mixture of 4 mL of a 25% aqueous solution of potassium hydroxide and 5 mL of ethylene glycol was dissolved 350 mg (0.66 mmol) of methyl 4-(4-hydroxy-4-(2-(2-acetoxyethoxy)phenyl)piperidino)-2,2-diphenylbutyrate. The resulting solution was stirred at 130° C. for 2 hours. Water was added to the reaction mixture, followed by neutralization with hydrochloric acid under ice cooling. The crystals thus precipitated were collected by filtration and dried, whereby 230 mg (yield: 73.4%) of 4-(4-hydroxy-4-(2-(2-hydroxyethoxy)phenyl)piperidino)-2, 2-diphenylbutyric acid was obtained.

$^1$H-NMR(CDCl$_3$) δ (ppm): 7.36(1H,dd), 7.20–7.32(10H,m), 7.21(1H,dd), 6.95(1H,dt), 6.89(1H,dd), 4.10(2H,t), 4.00(2H,t), 3.69(3H,s), 3.51(2H,s), 2.00–2.90 (10H,m), 1.90(2H,d).

Example 1

In 20 mL of anhydrous dimethylformamide were dissolved 3.5 g (10 mmol) of dimethyl(tetrahydro-3,3-diphenyl-2-furylidene)ammonium bromide and 1.93 g (10 mmol) of 4-(2-hydroxyphenyl)-4-piperidinol. To the resulting solution was added 3.2 g (30 mmol) of sodium carbonate, followed by stirring at 80° C. for 1.5 hours. The reaction mixture was distilled under reduced pressure to remove the solvent and the residue thus obtained was dissolved in ethyl acetate. The resulting solution was washed with water and dried. The residue obtained by concentrating the solvent under reduced pressure was purified by chromatography on a silica gel column, whereby 3.6 g (yield: 78.6%) of 4-(4-hydroxy-4-(2-hydroxyphenyl)piperidino)-N,N-dimethyl-2,2-diphenylbutaneamide (Compound No. 1) was obtained.

Example 2

In a similar manner to Example 1 except for the use of 4-(3-hydroxyphenyl)-4-piperidnol instead of 4-(2-hydroxyphenyl)-4-piperidinol, whereby 4-(4-hydroxy-4-(3-hydroxyphenyl)piperidino)-N,N-dimethyl-2,2-diphenylbutaneamide (Compound No. 2) (yield: 74.0%).

Example 3

In a similar manner to Example 1 except for the use of 4-(4-hydroxyphenyl)-4-piperidnol instead of 4-(2-hydroxyphenyl)-4-piperidinol, whereby 4-(4-hydroxy-4-(4-hydroxyphenyl)piperidino)-N,N-dimethyl-2,2-diphenylbutaneamide (Compound No. 3) was obtained (yield: 55.0%).

Example 4

In 20 mL of anhydrous dimethylformamide was dissolved 920 mg (2 mmol) of 4-(4-hydroxy-4-(2-hydroxyphenyl)piperidino)-N,N-dimethyl-2,2-diphenylbutaneamide. To the resulting solution were added 590 mg (3 mmol) of ethyl 4-bromo-n-butyrate, 414 mg (3 mmol) of potassium carbonate and a small amount of potassium iodide. The mixture was stirred under heating at 60° C. for 2 hours. After cooling, the reaction mixture was poured into water, followed by extraction with ethyl acetate, washing with water and drying. The solvent was distilled off under reduced pressure. The residue thus obtained was purified by chromatography on a silica gel, whereby 500 mg (yield: 43.7%) of ethyl 4-(2-(1-(4-dimethylamino-4-oxo-3,3-diphenylbutyl)-4-hydroxy-4-piperidinyl)phenoxybutyrate (Compound No. 4) was obtained.

Examples 5 to 24

Reaction was effected as in Example 4, whereby Compounds Nos. 5 to 24 as described in the below lists were obtained.

Example 25

In a liquid mixture of 5 mL of methanol and 5 mL of dioxane was dissolved 180 mg (0.32 mmol) of 4-(4-hydroxy-4-(2-(3-acetoxypropoxy)phenyl)piperidino)-N,N-dimethyl-2,2-diphenylbutaneamide. To the resulting solution, 5 mL of a 1N aqueous solution of sodium hydroxide was added. The resulting mixture was stirred at room temperature for 1 hour. Water was added to the reaction mixture, followed by extraction with chloroform, washing with water and drying. The residue obtained by distilling off the solvent was purified by chromatography on a silica gel column, whereby 150 mg (yield: 89.8%) of 4-(4-hydroxy-4-(2-(3-hydroxypropoxy)phenyl)piperidino)-N,N-dimethyl-2,2-diphenylbutaneamide (Compound No. 25) was obtained.

Examples 26 to 33

Reaction was effected as in Example 25, whereby Compounds Nos. 26 to 33 as described in the below list were obtained.

Example 34

In 10 mL of anhydrous dimethylformamide was dissolved 920 mg (2 mmol) of 4-(4-hydroxy-4-(2-hydroxyphenyl)piperidino)-N,N-dimethyl-2,2-diphenylbutaneamide. To the resulting solution were added 585 g (3 mmol) of 4-bromobutylacetate, 414 mg (3 mmol) of potassium carbonate and a small amount of potassium iodide. The resulting mixture was stirred under heating at 80° C. for 4 hours. After cooling, the reaction mixture was poured into water, followed by extraction with ethyl acetate, washing with water and drying. The residue obtained by distilling off the solvent under reduced pressure was dissolved in 15 mL of methanol. To the resulting solution was added 3 mL of a 1N aqueous solution of sodium hydroxide, followed by stirring at room temperature for 1 hour. From the reaction mixture, the solvent was distilled off under reduced pressure. The residue thus obtained was dissolved in chloroform. The resulting solution was washed with water and dried. The residue obtained by distilling off the solvent under reduced pressure was purified by chromatography on a silica gel column, whereby 260 mg (yield: 24.5%) of 4-(4-hydroxy-4-(2-(4-hydroxybutyloxy)phenyl)piperidino)-N,N-dimethyl-2,2-diphenylbutaneamide (Compound No. 34) was obtained.

Examples 35 and 36

Reaction was effected as in Example 34, whereby Compounds Nos. 35 and 36 as described in the below list were obtained.

Example 37

In 50 mL of anhydrous ether was dissolved 500 mg (0.9 mmol) of 4-(4-hydroxy-4-(2-(3-hydroxyhexyloxy)phenyl)piperidino)-N,N-dimethyl-2,2-diphenylbutaneamide (Compound No. 35). To the resulting solution was added 0.4 mL of a 4N solution of hydrochloric acid and dioxane under ice cooling and stirring. The white precipitate thus formed was collected by filtration, washed with ether and dried, whereby 460 mg (yield: 86.3%) of 4-(4-hydroxy-4-(2-(6-hydroxyhexyloxy)phenyl)piperidino)-N,N-dimethyl-2,2-diphenylbutaneamide hydrochloride (Compound No. 37) was obtained.

Examples 38 to 63

Reaction was effected as in Example 37, whereby Compounds Nos. 38 to 63 as described in the below lists were obtained.

Example 64

In a similar manner to Example 1 except for the use of diethyl(tetrahydro-3,3-diphenyl-2-furylidene)ammonium bromide instead of dimethyl (tetrahydro-3,3-diphenyl-2-furilydene)ammonium bromide, whereby 4-(4-hydroxy-4-

(2-hydroxyphenyl)piperidino)-N,N-diethyl-2,2-diphenylbutaneamide (Compound No. 64) was obtained (yield: 66.0%).

Example 65

In a similar manner to Example 1 except for the use of (tetrahydro-3,3-diphenyl-2-furylidene)pyrrolidinium bromide instead of dimethyl(tetrahydro-3,3-diphenyl-2-furilydene)ammonium bromide, whereby 4-(4-hydroxy-4-(2-hydroxyphenyl)piperidino)-2,2-diphenyl-1-(1-pyrrolidinyl)-1-butanone (Compound No. 65) was obtained (yield: 99.0%).

Example 66

Reaction was effected as in Example 4, whereby Compound No. 66 as described in the below list was obtained.

Examples 67 and 68

Reaction was effected as in Example 25, whereby Compounds Nos. 67 and 68 as described in the below list were obtained.

Example 69

In 140 mL of anhydrous dimethylformamide was dissolved 20.8 g (43 mmol) of 4-(4-hydroxy-4-(2-hydroxyphenyl)piperidino)-2,2-diphenyl-1-(1-pyrrolidinyl)-1-butanone (Compound No. 65). To the resulting solution was added 3.85 g of potassium hydroxide (powder). The resulting mixture was stirred at room temperature for 0.5 hour. To the reaction mixture was added dropwise 7.9 g (47 mmol) of ethyl bromoacetate under ice cooling and stirring, followed by stirring at the same temperature for 10 minutes. After the reaction mixture was poured into water, extraction was effected with ethyl acetate. The extract was washed with water and then, dried. The solvent was distilled off under reduced pressure. The residue thus obtained was purified by chromatography on a silica gel column, followed by crystallization from toluene, whereby 18.0 g (yield: 73.6%) of ethyl 2-(2-(1-(4-pyrrolidino-4-oxo-3,3-diphenylbutyl)-4-hydroxy-4-piperidinyl)phenoxyacetate (Compound No. 69) was obtained.

Example 70

In 15 mL of methanol was dissolved 780 mg (1.4 mmol) of ethyl-(2-(1-(4-dimethylamino-4-oxo-3,3-diphenylbutyl)-4-hydroxy-4-piperidinyl)phenoxyacetate (Compound No. 53). To the resulting solution was added 5 mL of a 1N aqueous solution of sodium hydroxide. The resulting mixture was stirred at room temperature for 1 hour. After the reaction mixture was concentrated, water was added. The resulting mixture was then neutralized with 0.3 mL of acetic acid, followed by extraction with chloroform, washing with water and drying. The residue obtained by distilling off the solvent was crystallized from acetone, whereby 580 mg of 2-(2-(1-(4-dimethylamino-4-oxo-3,3-diphenylbutyl)-4-hydroxy-4-piperidinyl)phenoxyacetic acid (Compound No. 70) was obtained (yield: 80.3%).

Example 71

In a similar manner to Example 70 except for the use of ethyl 2-(2-(1-(4-pyrrolidino-4-oxo-3,3-diphenylbutyl)-4-hydroxy-4-piperidinyl)phenoxyacetate (Compound No. 69) instead of ethyl 2-(2-(1-(4-dimethylamino-4-oxo-3,3-diphenylbutyl)-4-hydroxy-4-piperidinyl)phenoxyacetate, whereby 2-(2-(1-(4-pyrrolidino-4-oxo-3,3-diphenylbutyl)-4-hydroxy-4-piperidinyl)phenoxyacetic acid (Compound No. 71) was obtained (yield: 81.0%).

Example 72

In a liquid mixture of 30 mL of a 40% aqueous solution of potassium hydroxide and 40 mL of ethylene glycol was dissolved 817 mg (1.64 mmol) of 4-(4-hydroxy-4-(2-(2-acetoxyethoxy)phenyl)piperidino)-2,2-diphenylbutylonitrile. The resulting solution was stirred at 170° C. for 20 hours. After the addition of water, extraction was conducted with chloroform. The extract was washed with water and then dried. The residue obtained by distilling off the solvent under reduced pressure was purified by chromatography on a silica gel column, whereby 271 mg (yield: 34.9%) of 4-(4-hydroxy-4-(2-(2-hydroxyethoxy)phenyl)piperidino)-2,2-diphenylbutaneamide (Compound No. 72) was obtained.

Example 73

In 5 mL of anhydrous dimethylformamide was dissolved 81 mg (0.17 mmol) of 4-(4-hydroxy-4-(2-(2-acetoxyethoxy)phenyl)piperidino)-2,2-diphenylbutyric acid. The resulting solution was stirred at room temperature for 1 hour. To the reaction mixture were added 36 mg (0.22 mmol) of carbodiimidazole, and after one hour 16 mg (0.22 mmol) of n-butylamine. After stirring at 70° C. for 24 hours, stirring was conducted for further 3 hours at 130° C., whereby the reaction was completed. Water was added to the reaction mixture, followed by extraction with ethyl acetate, washing with water and drying. The residue obtained by distilling off the solvent under reduced pressure was purified by chromatography on an alumina column and then chromatography on a silica gel column, whereby 35 mg (yield: 38.9%) of 4-(4-hydroxy-4-(2-(2-hydroxyethoxy)phenyl)piperidino)-N-butyl-2,2-diphenylbutaneamide (Compound No. 73) was obtained.

Examples 74 to 81

The reaction was conducted as in Example 37, whereby compounds Nos. 74 to 81 were obtained.

TABLE 1

Compound List

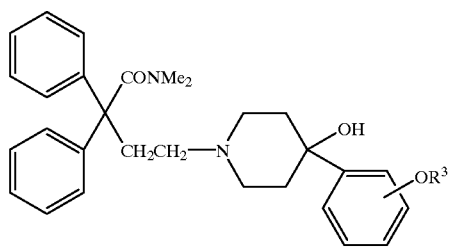

| Comp'd No. | OR³ | Yield (%) | Properties | Melting point (° C.) (decomposed) |
|---|---|---|---|---|
| 1 | 2-OH | 78.6 | Yellowish white amorphous substance | |
| 2 | 3-OH | 74.0 | White crystals | 169 |

TABLE 1-continued

Compound List

| Comp'd No. | OR³ | Yield (%) | Properties | Melting point (° C.) (decomposed) |
|---|---|---|---|---|
| 3 | 4-OH | 55.0 | Yellowish white powder | 155 |
| 4 | 2-O(CH₂)₃COOEt | 43.7 | Yellow viscous liquid | |
| 5 | 2-OCH₂COOEt | 49.0 | White amorphous substance | |
| 6 | 2-O(CH₂)₅COOEt | 58.3 | Yellow viscous liquid | |
| 7 | 2-OC(CH₃)₂COOEt | 27.4 | Yellow viscous liquid | |
| 8 | 3-OCH₂COOEt | 10.0 | Yellow viscous liquid | |
| 9 | 3-O(CH₂)₃COOEt | 47.0 | Yellow viscous liquid | |
| 10 | 3-O(CH₂)₅COOEt | 55.0 | Yellow viscous liquid | |
| 11 | 4-OCH₂COOEt | 17.0 | White powder | |
| 12 | 4-O(CH₂)₃COOEt | 35.0 | Colorless viscous liquid | |
| 13 | 4-O(CH₂)₅COOEt | 27.0 | Colorless viscous liquid | |
| 14 | 2-O(CH₂)₂OAc | 64.3 | Colorless viscous liquid | |
| 15 | 2-O(CH₂)₃OAc | 63.0 | White amorphous substance | |
| 16 | 3-O(CH₂)₂OAc | 55.0 | Yellow viscous liquid | |
| 17 | 3-O(CH₂)₃OAc | 44.0 | Yellow viscous liquid | |
| 18 | 3-O(CH₂)₄OAc | 59.0 | Yellow viscous liquid | |
| 19 | 3-O(CH₂)₆OAc | 20.0 | Yellow viscous liquid | |
| 20 | 4-O(CH₂)₃OAc | 48.0 | Colorless viscous liquid | |

TABLE 2

Compound List

| Comp'd No. | OR³ | Yield (%) | Properties | Melting point (° C.) (decomposed) |
|---|---|---|---|---|
| 21 | 4-O(CH₂)₄OAc | 40.0 | Colorless viscous liquid | |
| 22 | 4-O(CH₂)₆OAc | 38.0 | Colorless viscous liquid | |
| 23 | 2-OCH₂CONH₂ | 33.0 | White amorphous substance | |
| 24 | 2-O(CH₂)₂OMe | 53.0 | White amorphous substance | |
| 25 | 2-O(CH₂)₃OH | 89.8 | White amorphous substance | |
| 26 | 2-O(CH₂)₂OH | 49.8 | White amorphous substance | |
| 27 | 3-O(CH₂)₂OH | 74.0 | White amorphous substance | |
| 28 | 3-O(CH₂)₃OH | 90.0 | Colorless viscous liquid | |
| 29 | 3-O(CH₂)₄OH | 84.0 | Colorless viscous liquid | |

TABLE 2-continued

Compound List

| Comp'd No. | OR³ | Yield (%) | Properties | Melting point (° C.) (decomposed) |
|---|---|---|---|---|
| 30 | 3-O(CH₂)₆OH | 81.0 | Colorless viscous liquid | |
| 31 | 4-O(CH₂)₃OH | 97.0 | Colorless viscous liquid | |
| 32 | 4-O(CH₂)₄OH | 84.0 | Colorless viscous liquid | |
| 33 | 4-O(CH₂)₆OH | 55.0 | Colorless viscous liquid | |
| 34 | 2-O(CH₂)₄OH | 24.5 | Colorless viscous liquid | |
| 35 | 2-O(CH₂)₆OH | 50.0 | White amorphous substance | |
| 36 | 4-O(CH₂)₂OH | 11.0 | Colorless viscous liquid | |

TABLE 3

Compound List

| Comp'd No. | OR³ | Yield (%) | Properties | Melting point (° C.) (decomposed) |
|---|---|---|---|---|
| 37 | 2-O(CH₂)₆OH | 86.3 | White powder | 110 |
| 38 | 2-OH | 52.9 | Yellowish white powder | 150 |
| 39 | 2-O(CH₂)₂OAc | 84.3 | Yellowish white powder | 105 |
| 40 | 2-O(CH₂)₃OAc | 56.3 | White powder | 120 |
| 41 | 2-O(CH₂)₂OH | 72.0 | White powder | 131 |
| 42 | 2-O(CH₂)₃OH | 77.8 | White powder | 140 |
| 43 | 2-O(CH₂)₄OH | 59.0 | White powder | 110 |
| 44 | 2-(OCH₂)₂OMe | 87.0 | White powder | 110 |
| 45 | 3-O(CH₂)₂OH | 72.0 | White powder | 113 |
| 46 | 3-O(CH₂)₃OH | 81.0 | White powder | 118 |
| 47 | 3-C(CH₂)₄OH | 83.0 | White powder | 128 |
| 48 | 3-O(CH₂)₆OH | 73.0 | White powder | 106 |
| 49 | 4-O(CH₂)₂OH | 48.8 | Yellowish white powder | 121 |
| 50 | 4-O(CH₂)₃OH | 52.0 | Yellowish white powder | 123 |
| 51 | 4-O(CH₂)₄OH | 52.7 | Yellowish white powder | 117 |
| 52 | 4-O(CH₂)₆OH | 61.0 | Yellowish white powder | 97 |
| 53 | 2-OCH₂COOEt | 71.4 | White powder | 118 |
| 54 | 2-O(CH₂)₃COOEt | 65.7 | Yellowish white powder | 105 |
| 55 | 2-O(CH₂)₅COOEt | 53.8 | Yellowish white powder | 80 |
| 56 | 2-OC(CH₃)₂COOEt | 70.4 | Yellowish white powder | 115 |

TABLE 4

Compound List

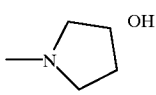

| Comp'd No. | OR³ | Yield (%) | Properties | Melting point (° C.) (decomposed) |
|---|---|---|---|---|
| 57 | 2-OCH₂CO NH₂ | 93.3 | White powder | 120 |
| 58 | 3-OCH₂COOEt | 68.0 | White powder | 118 |
| 59 | 3-O(CH₂)₃COOEt | 78.0 | Yellowish white powder | 88 |
| 60 | 3-O(CH₂)₅COOEt | 69.0 | Yellowish white powder | 86 |
| 61 | 4-OCH₂COOEt | 64.0 | White powder | 105 |
| 62 | 4-O(CH₂)₃COOEt | 61.1 | Yellowish white powder | 97 |
| 63 | 4-O(CH₂)₅COOEt | 43.7 | Yellowish white powder | 73 |

TABLE 5

Compound List

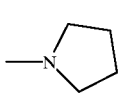

| Comp'd No. | NR₁R₂ | OR³ | Yield (%) | Properties | Melting point (° C.) (decomposed) |
|---|---|---|---|---|---|
| 64 | NEt₂ | OH | 66.0 | Yellow oil | |
| 65 | pyrrolidinyl | OH | 99.0 | Yellowish white amorphous substance | |
| 66 | NEt₂ | OCH₂COOEt | 20.0 | Yellowish white amorphous substance | |
| 67 | NEt₂ | OCH₂CH₂OH | 43.2 | Yellowish white amorphous substance | |
| 68 | pyrrolidinyl | OCH₂CH₂OH | 47.5 | White amorphous substance | |

TABLE 5-continued

Compound List

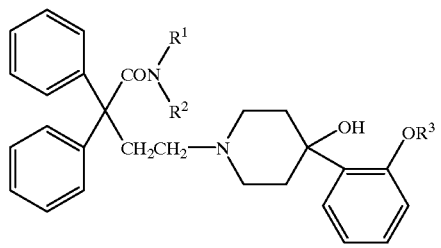

| Comp'd No. | NR₁R₂ | OR³ | Yield (%) | Properties | Melting point (° C.) (decomposed) |
|---|---|---|---|---|---|
| 69 | pyrrolidinyl | OCH₂COOEt | 73.6 | White powder | 129–131 |
| 70 | NMe₂ | OCH₂COOH | 80.3 | White powder | 161–164 |
| 71 | pyrrolidinyl | OCH₂COOH | 81.0 | White powder | 239–240 |
| 72 | NH₂ | OCH₂CH₂OH | 34.9 | Yellow oil | |
| 73 | NH-n-Bu | OCH₂CH₂OH | 38.9 | White powder | 130–131 |

TABLE 6

Compound List

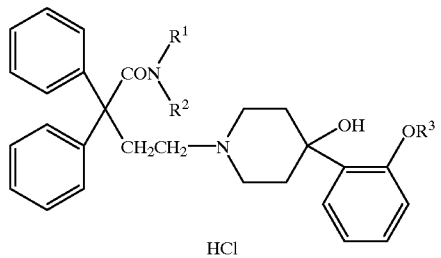

HCl

| Comp'd No. | NR₁R₂ | OR³ | Yield (%) | Properties | Melting point (° C.) (decomposed) |
|---|---|---|---|---|---|
| 74 | NEt₂ | OCH₂COOEt | 71.0 | White powder | 118 |
| 75 | NEt₂ | OCH₂CH₂OH | 45.0 | White powder | 130 |
| 76 | pyrrolidinyl | OCH₂CH₂OH | 62.0 | White powder | 145 |
| 77 | pyrrolidinyl | OCH₂COOEt | 81.0 | White powder | 120 |
| 78 | NMe₂ | OCH₂COOH | 97.4 | White powder | 175–176 |

TABLE 6-continued

Compound List

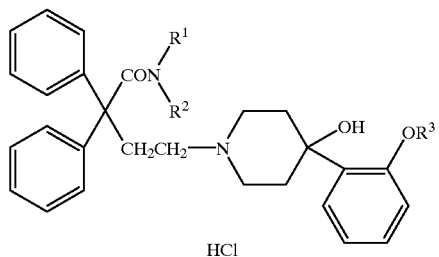

HCl

| Comp'd No. | NR₁R₂ | OR³ | Yield (%) | Properties | Melting point (° C.) (decom-posed) |
|---|---|---|---|---|---|
| 79 | ![pyrrolidine] | OCH₂COCH | 87.2 | White powder | 155–160 |
| 80 | NH₂ | OCH₂CH₂OH | 52.0 | White powder | 144 |
| 81 | NH-n-Bu | OCH₂CH₂OH | 99.0 | White powder | 104 |

TABLE 7

| Comp'd No. | Mass (FAB: (M + H)⁺) | $^1$H-NMR δ:ppm (measured in CDCl₃ unless specifically indicated) |
|---|---|---|
| 1 | 459 | 7.20–7.50(11H, m), 7.11(1H, ddd), 7.05(1H, dd), 6.75–6.82(2H, m), 2.90(1H, br. s), 2.89(3H, br. s), 2.65–2.75(2H, m), 2.20–2.50(7H, m), 2.00–2.20(4H, m), 1.93(2H, d) |
| 2 | 459 | in DMSO-d₆: 9.11(1H, s), 7.25–7.50(10H, m), 7.05(1H, t), 6.85(1H, t), 6.80(1H, d), 6.58(1H, dd), 4.55 (1H, br. s), 2.40–3.20(6H, br.), 2.50–2.60(2H, m), 2.20–2.50(4H, m), 2.00–2.20(2H, m), 1.70–1.90 (2H, m), 1.48(2H, d) |
| 3 | 459 | in DMSO-d₆: 9.21(1H, s), 7.30–7.50(10H, m), 7.20(2H, d), 6.71(2H, d), 5.00(1H, br. s), 2.00–3.60(16H, m), 1.66(2H, d) |
| 4 | 573 | 7.15–7.50(12H, m), 6.85–6.95(2H, m), 4.14(2H, q), 4.08(2H, t), 3.99(1H, s), 2.98(3H, br. s), 2.60–2.70(2H, m), 2.48(2H, t), 2.20–2.60(7H, m), 1.80–2.20(8H, m), 1.25(3H, t) |
| 5 | 545 | 7.25–7.50(11H, m), 7.18(1H, ddd), 6.95(1H, ddd), 6.75(1H, dd), 4.64(2H, s), 4.35(1H, s), 4.27(2H, q), 2.98(3H, br. s), 2.60–2.70(2H, m), 2.40–2.60(4H, m), 2.35(3H, br. s), 2.10–2.20(2H, m), 1.90–2.10(4H, m), 1.29(3H, t) |
| 6 | 601 | 7.15–7.50(12H, m), 6.85–6.95(2H, m), 4.13(1H, s), 4.12(2H, q), 4.03(2H, t), 2.98(3H, br. s), 2.60–2.70(2H, m), 2.20–2.60(7H, m), 2.32(2H, t), 2.10–2.20(2H, m), 1.90–2.10(4H, m), 1.80–1.90(2H, quintet), 1.65–1.80(2H, quintet), 1.45–1.55(2H, m), 1.25(3H, t) |
| 7 | 573 | 7.25–7.50(10H, m), 7.24(1H, dd), 7.13(1H, dt), 6.94(1H, t), 6.69(1H, d), 4.75(1H, br. s), 4.18(2H, q), 3.10–3.40 (4H, br.), 3.00(3H, s), 2.50–2.90 (6H, m), 2.31(3H, s), 2.18(2H, d), 1.70(6H, s), 1.15(3H, t) |
| 8 | 545 | 7.20–7.50(11H, m), 7.00–7.10(2H, m), 6.76(1H, dd), 4.60(2H, s), 4.26(2H, q), 2.98(3H, br. s), 2.60–2.80(2H, m), 2.20–2.60(7H, m), 2.00–2.20(4H, m), 1.50–1.70(3H, m), 1.28(3H, t) |
| 9 | 573 | 7.20–7.50(11H, m), 6.95–7.05(2H, m), 6.74(1H, dd), 4.13(2H, q), 3.98(2H, t), 2.98(3H, br. s), 2.60–2.80(2H, m), 2.20–2.60(7H, m), 2.49(2H, t), 2.00–2.20(6H, m), 1.63(2H, d), 1.56(1H, s), 1.25 (3H, t) |

TABLE 8

| Comp'd No. | Mass (FAB: (M + H)⁺) | $^1$H-NMR δ:ppm (measured in CDCl₃ unless specifically indicated) |
|---|---|---|
| 10 | 601 | 7.20–7.50(11H, m), 6.95–7.05(2H, m), 6.74(1H, dd), 4.12(2H, q), 3.93(2H, t), 2.98(3H, br. s), 2.60–2.80(2H, m), 2.20–2.60(7H, m), 2.32(2H, t), 2.00–2.20(4H, m), 1.60–1.80(6H, m), 1.40–1.60 (2H, m), 1.25(3H, t) |
| 11 | 545 | 7.20–7.50(12H, m), 6.80–6.85(2H, m), 4.58(2H, s), 4.25(2H, q), 2.95(3H, br. s), 2.65–2.85(2H, m), 2.00–2.60(8H, m), 2.32(3H, br. s), 1.65(2H, d), 1.28(3H, td), |
| 12 | 573 | 7.20–7.50(12H, m), 6.82(2H, d), 4.13(2H, q) 3.98(2H, t), 2.98(3H, br. s), 2.65–2.75(2H, m), 2.45–2.55(2H, m), 2.49(2H, t), 2.20–2.50(5H, m), 1.95–2.20(6H, m), 1.64(2H, d), 1.48(1H, br. s), 1.24(3H, t) |
| 13 | 601 | 7.20–7.50(12H, m), 6.82(2H, d), 4.12(2H, q), 3.93 (2H, t), 2.98(3H, br. s), 2.65–2.75(2H, m), 2.55–2.65 (2H, m), 2.20–2.60(5H, m), 2.32(2H, t), 2.10–2.20 (2H, m), 2.03(2H, ddd), 1.78(2H, quintet), 1.60–1.75 (4H, m), 1.45–1.55(3H, m), 1.25(3H, t) |
| 14 | 545 | 7.15–7.50(12H, m), 6.94(1H, t), 6.85(1H, d), 4.45 (2H, t), 4.22(2H, t), 3.95(1H, br. s), 2.99(3H, br. s), 1.90–2.80(13H, m), 2.08(3H, s), 1.70–1.90(2H, m) |
| 15 | 559 | 7.15–7.50(12H, m), 6.93(1H, t), 6.89(1H, d), 4.24 (2H, t), 4.13(2H, t), 4.05(1H, br. s), 2.98(3H, br. s), |

TABLE 8-continued

| Comp'd No. | Mass (FAB: (M + H)+) | ¹H-NMR δ:ppm (measured in CDCl₃ unless specifically indicated) |
|---|---|---|
| 16 | 545 | 1.90–2.80(13H, m), 2.15(2H, quintet), 2.06(3H, s), 1.60–1.90(2H, m) 7.00–7.50(13H, m), 6.80(1H, d), 4.10–4.50(4H, m), 3.10–3.40(4H, m), 2.95(3H, br. s), 2.28(3H, br. s), 2.08(3H, s), 2.40–3.10(6H, m), 1.80(2H, d) |
| 17 | 559 | 7.00–7.50(13H, m), 6.75(1H, d), 4.24(2H, t), 4.03 (2H, t), 2.95(3H, br. s), 2.00–3.00(15H, m), 2.04 (3H, s), 1.80(2H, d) |
| 18 | 573 | 7.00–7.50(13H, m), 6.80(1H, d), 3.90–4.20(4H, m), 2.00–3.20(16H, m), 2.03(3H, s), 1.60–2.00(6H, m) |
| 19 | 601 | 7.00–7.60(13H, m), 6.80(1H, d), 3.80–4.20(4H, m), 2.60–3.50(10H, m), 2.98(3H, br. s), 2.29(3H, br. s), 2.03(3H, s), 1.20–2.20(10H, m) |

TABLE 9

| Comp'd No. | Mass (FAB: (M + H)+) | ¹H-NMR δ:ppm (measured in CDCl₃ unless specifically indicated) |
|---|---|---|
| 20 | 559 | 7.20–7.60(12H, m), 6.83(2H, d), 4.24(2H, t), 4.02(2H, t), 1.60–3.20(21H, m), 2.04(3H, s) |
| 21 | 573 | 7.20–7.50(12H, m), 6.83(2H, d), 3.80–4.25(4H, m), 2.10–3.20(17H, m), 2.04(3H, s), 1.80–2.00(8H, m) |
| 22 | 601 | 7.20–7.50(12H, m), 6.83(2H, d), 4.06(2H, t), 3.93(2H, t), 2.98(3H, br. s), 2.60–2.80(2H, m), 2.45–2.55(2H, m), 2.20–2.50(5H, m), 2.00–2.20 (4H, m), 2.04(3H, s), 1.70–1.90(2H, m), 1.60–1.70 (4H, m), 1.35–1.55(4H, m) |
| 23 | 516 | 8.37(1H, br. s), 7.54(1H, dd), 7.20–7.50(11H, m), 7.01(1H, d), 6.81(1H, d), 6.48(1H, br. s), 4.53(2H, s), 3.00(3H, br. s), 2.65–2.75(4H, m) 2.40–2.50(2H, m), 2.33(3H, br. s), 2.10–2.20(2H, m), 1.90–2.00(2H, m), 1.55(2H, d) |
| 24 | 517 | 7.30–7.50(10H, m), 7.23(1H, dd), 7.18(1H, ddd), 6.91 (1H, dd), 6.87(1H, d), 4.31(1H, s), 4.15(2H, dd), 3.71(2H, dd), 3.40(3H, s), 2.98(3H, br. s), 2.65–2.75(2H, m), 2.40–2.60(4H, m), 2.35(3H, br. s), 2.10–2.20(2H, m), 1.95–2.10(4H, m) |
| 25 | 516 | 7.25–7.50(11H, m), 7.19(1H, ddd), 6.85–6.95(2H, m), 4.15(2H, t), 3.83(2H, t), 3.56(1H, s), 2.98(3H, br. s), 2.90(1H, br. s), 2.60–2.70(2H, m), 2.20–2.55(7H, m), 2.10–2.30(4H, m), 2.04(2H, quintet), 1.86(2H, d) |
| 26 | 503 | 7.25–7.50(11H, m), 7.19(1H, ddd), 6.93(1H, ddd), 6.87(1H, d), 4.44(1H, br. s), 4.06(2H, t), 3.95(2H, br. t), 2.98(3H, m), 2.93(3H, br. s), 2.40–2.60(4H, m), 2.20–2.50(5H, m), 2.00–2.15(2H, m), 1.67(2H, d) |
| 27 | 503 | 7.25–7.50(10H, m), 7.22(1H, dd), 7.07(1H, dd), 7.05(1H, d), 6.77(1H, dd), 4.06(2H, t), 3.93(2H, t), 2.98(3H, br. s), 2.65–2.75(2H, m), 2.40–2.55(2H, m), 2.20–2.50(5H, m), 2.10–2.20(2H, m), 2.06(2H, ddd), 1.63(2H, d) |
| 28 | 517 | 7.20–7.50(10H, m), 7.21(1H, dd), 7.00–7.10(2H, m), 6.76(1H, dd), 4.11(2H, t), 3.84(2H, t), 2.98(3H, br. s), 2.60–2.80(2H, m), 2.40–2.50(2H, m), 2.20–2.50(5H, m), 2.02(2H, quintet), 2.00–2.20(7H, m), 1.62(2H, d) 1.60(1H, s) |

TABLE 10

| Comp'd No. | Mass (FAB: (M + H)+) | ¹H-NMR δ:ppm (measured in CDCl₃ unless specifically indicated) |
|---|---|---|
| 29 | 531 | 7.25–7.50(10H, m), 7.21(1H, dd), 7.00–7.10(2H, m), 6.75(1H, dd), 3.98(2H, t), 3.70(2H, t), 2.98(3H, br. s), 2.65–2.75(2H, m), 2.45–2.55(2H, m), 2.20–2.50(5H, m), 1.95–2.20(4H, m), 1.80–1.90(2H, m), 1.70–1.80 (2H, m), 1.65(1H, s), 1.63(2H, d) |
| 30 | 559 | 7.20–7.50(10H, m), 7.21(H1, dd), 7.00–7.10(2H, m), 6.75(1H, dd), 3.94(2H, t), 3.64(2H, t), 2.98(3H, br. s) 2.65–2.75(2H, m), 2.20–2.60(7H, m), 2.00–2.20(4H, m), 1.40–1.90(12H, m) |
| 31 | 517 | 7.20–7.50(12H, m), 6.84(2H, d), 4.09(2H, t), 3.84(2H, t), 2.98(3H, br. s), 2.65–2.75(2H, m), 2.20–2.60(7H, m), 1.90–2.20(6H, m), 1.64(2H, d), 1.56(1H, br. s) |
| 32 | 531 | 7.20–7.50(12H, m), 6.83(2H, d), 3.97(2H, t), 3.69(2H, t), 2.98(3H, br. s), 2.65–2.75(2H, m), 2.20–2.60(7H, m), 1.90–2.20(4H, m), 1.86(2H, quintet), 1.73(2H, quintet), 1.65(2H, d) |
| 33 | 559 | 7.20–7.50(12H, m), 6.83(2H, d), 3.93(2H, t), 3.64(2H, t), 3.47(1H, s), 2.98(3H, br. s), 2.65–2.75(2H, m), 2.20–2.60(7H, m), 2.10–2.20(2H, m), 2.04(2H, ddd), 1.77(2H, quintet), 1.65(2H, d), 1.59(2H quintet), 1.35–1.55(4H, m) |
| 34 | 531 | 7.20–7.50(11H, m), 7.19(1H, ddd), 6.91(1H, dd), 6.87(1H, d), 4.05(2H, t), 3.70(2H, t), 3.50(1H, s), 2.98(3H, br. s), 2.65–2.75(2H m), 2.10–2.60(11H, m), 1.80–2.00(2H, m), 1.81(2H, d), 1.70–1.80(2H, m) |
| 35 | 559 | 7.15–7.50(12H, m), 6.85–6.95(2H, m), 4.10(1H, s), 4.03(2H, t), 3.66(2H, br. t), 2.97(3H, br. s), 2.65–2.75(2H, m), 2.40–2.60(6H, m), 2.34(3H, br. s), 1.90–2.20(6H, m), 1.82(2H, quintet), 1.61(2H, quintet), 1.40–1.60(4H, m) |
| 36 | 503 | 7.20–7.50(12H, m), 6.85(2H, d), 4.05(2H, t), 3.93(2H, t), 2.98(3H, br. s), 2.65–2.75(2H, m), 2.45–2.55(2H, m), 2.20–2.40(5H, m), 2.10–2.20(2H, m), 2.04(2H ddd), 1.64(2H, d), 1.55(1H, br. s) |

TABLE 11

| Comp'd No. | Mass (FAB: (M + H)+) | ¹H-NMR δ:ppm (measured in CDCl₃ unless specifically indicated) |
|---|---|---|
| 37 | 559 | in DMSO-d₆: 10.7, 10.4(total 1H, each br. s), 7.30–7.60(11H, m), 7.19–7.24(1H, m), 6.98(1H, d), 6.91(1H, dd), 5.32, 5.12(total 1H, each s), 4.29(1H, br. s), 3.95–4.10(2H, m), 3.20–3.50(4H, m), 2.80–3.20(2H, m), 2.93(3H, br. s), 2.67(4H, s), 2.50–2.80(2H, m), 2.25(3H, br. s), 1.81(2H, quintet), 1.71(2H, d), 1.30–1.50(6H, m) |
| 38 | 459 | in DMSO-d₆: 10.6, 10.2(total 1H, each br. s), 9.74, 9.55(total 1H, each s), 7.20–7.60(11H, m), 7.07(1H, d), 6.87, 6.83(total 1H, each d), 6.77(1H, dd), 5.61, 5.40(total 1H, each br. s), 3.20–3.40(2H, m), 2.90–3.20(2H, m), 2.91(3H, br. s), 2.67(4H, s), 2.60–2.80(2H, m), 2.25(3H, br. s), 1.72, 1.40(total 2H, each d) |
| 39 | 545 | in DMSO-d₆: 10.6, 10.3(total 1H, each br. s), 7.30–7.60(11H, m), 7.24(1H, dd), 7.01(1H, d), 6.95(1H, dd), 5.34, 5.10(total 1H, each s), 4.45, 4.33(total 2H, each t), 4.24, 4.20(total 2H, each t), 3.20–3.60(2H, m), 2.90–3.20(2H, m), 2.94(3H, br. s), 2.68(4H, s), 2.55–2.75(2H, m), 2.24(3H, br. s), 2.00, 1.85(total 3H, each s), 1.72, 1.41(total 2H, each d) |
| 40 | 559 | in DMSO-d₆: 10.2, 9.86(total 1H, each br. s), 7.30–7.60(11H, m), 7.23(1H, ddd), 6.99(1H, d), 6.93(1H, dd), 5.32, 5.19(total 1H, each s), 4.17, 4.13(total 1H, each t), 4.08(2H, t), 3.20–3.50(2H, m), 3.00–3.20(2H, m), 2.94(3H, br. s), 2.67(4H, s), 2.50–2.70(2H, m), 2.25(3H, br. s), 2.16(2H, quintet), 2.02, 1.99(total 3H, each s), 1.68, 1.42(total 2H, each d) |

TABLE 11-continued

| Comp'd No. | Mass (FAB: (M + H)+) | 1H-NMR δ:ppm (measured in CDCl3 unless specifically indicated) |
|---|---|---|
| 41 | 503 | in DMSO-d6: 10.5, 10.3(total 1H, each br. s), 7.30–7.60(11H, m), 7.18–7.26(1H, m), 7.01, 6.96(total 1H, each d), 6.92(1H, dd), 5.33, 5.27(total 1H, each s), 5.12, 4.76(total 1H, each br. s), 4.03, 3.97(total 2H, each t), 3.78, 3.65(total 2H, each br.t), 3.20–3.50(2H, m), 2.93(3H, br. s), 2.60–3.20(8H, m), 2.25(3H, br. s), 1.61, 1.44(total 2H, each d) |

TABLE 12

| Comp'd No. | Mass (FAB: (M + H)+) | 1H-NMR δ:ppm (measured in CDCl3 unless specifically indicated) |
|---|---|---|
| 42 | 517 | in DMSO-d6: 10.6, 10.3(total 1H, each br. s), 7.30–7.60 (11H, m), 7.18–7.26(1H, m), 6.87–7.02(2H, m), 5.34, 5.24(total 1H, each s), 4.60(1H, br. s), 4.00–4.15(2H, m), 3.55(2H, t), 3.20–3.50(2H, m), 2.94(3H, br. s), 2.50–3.20(8H, m), 2.25(3H, br. s), 1.96, 1.84(total 2H, each quintet), 1.69, 1.42(total 2H, each d) |
| 43 | 531 | in DMSO-d6: 10.7, 10.4(total 1H, each br. s), 7.30–7.60(11H, m), 7.21(H1, dd), 6.98(H1, d), 6.90(1H, dd), 5.30, 5.15(total 1H, each br. s), 4.40(1H, br. s), 4.00–4.10(2H, m), 3.20–3.50(4H, m), 2.90–3.20(2H, m), 2.93(3H, br. s), 2.68(4H, s), 2.50–2.80(2H, m), 2.25(3H, br. s), 1.85, 1.71(total 2H, each quintet), 1.70, 1.40(total 2H, each d), 1.54(2H, quintet) |
| 44 | 517 | in DMSO-d6: 10.5, 10.4(total 1H, each br. s), 7.30–7.60(11H, m), 7.23(1H, ddd), 6.98–7.04(1H, m), 6.90–6.96(1H, m), 5.30, 5.10(total 1H, each s), 4.17, 4.14(total 2H, each t), 3.77, 3.58(total 2H, each t), 3.31, 3.21(total 3H, each s), 3.20–3.40(2H, m), 2.90–3.20(2H, m), 2.93(3H, br. s), 2.55–2.75(6H, m), 2.25(3H, br. s), 1.75, 1.40(total 2H, each d) |
| 45 | 503 | in DMSO-d6: 10.7(1H, br. s), 7.30–7.50(10H, m), 7.24(1H, dd), 7.01(1H, dd), 6.98(1H, d), 6.81(1H, dd), 5.33(1H, s), 4.80(1H, br. s), 3.97(2H, t), 3.70(2H, t), 3.20–3.40(2H, m), 2.90–3.10(2H, m), 2.92(3H, br. s), 2.68(4H, s), 2.38(2H, ddd), 2.25(3H, br. s), 1.69 (2H, d) |
| 46 | 517 | in DMSO-d6: 10.7(1H, br. s), 7.30–7.50(10H, m), 7.23(1H, dd), 7.00(1H, d), 6.97(1H, d), 6.80(1H, dd), 5.33(1H, s), 4.49(1H, br. s), 4.02(2H, t), 3.55(2H, t), 3.20–3.40(2H, m), 2.90–3.10(2H, m), 2, 92(3H, br. s), 2.68(4H, s), 2.38(2H, ddd), 2.25(3H, br. s), 1.85(2H, quintet), 1.69(2H, d) |
| 47 | 531 | in DMSO-d6: 10.6(1H, br. s), 7.30–7.50(10H, m), 7.23(H1, dd), 6.98–7.02(1H, m), 6.96(1H, d), 6.79(1H, dd), 5.32(1H, s), 4.37(1H, br. s), 3.95(2H, t), 3.44(2H, t), 3.20–3.40(2H, m), 2.90–3.10(2H, m) 2.93(3H, br. s), 2.68(4H, s), 2.38(2H, ddd), 2.25(3H, br. s), 1.60–1.80(4H, m), 1.55(2H, quintet) |

TABLE 13

| Comp'd No. | Mass (FAB: (M + H)+) | 1H-NMR δ:ppm (measured in CDCl3 unless specifically indicated) |
|---|---|---|
| 48 | 559 | in DMSO-d6: 10.6(1H, br. s), 7.30–7.50(10H, m), 7.24(1H, dd), 6.98–7.02(1H, m), 6.96(1H, d), 6.79(1H, dd), 5.32(1H, s), 4.28(1H, br. s), 3.94(2H, t), 3.39(2H, t), 3.20–3.40(2H, m), 2.90–3.10(2H, m), 2.93(3H, br. s), 2.68(4H, s), 2.37(2H, ddd), 2.25(3H, br. s), 1.60–1.75(4H, m), 1.30–1.50(6H, m) |
| 49 | 503 | in DMSO-d6: 10.6(1H, br. s), 7.25–7.50(12H, m), 6.89(2H, d), 5.22(1H, s), 4.77(1H, br. s), 3.96(2H, t), 3.69(2H, br, t), 3.20–3.40(2H, m), 2.90–3.20(2H, m), 2.92(3H, br, s), 2.67 (4H, s), 2.00–2.50 (5H, m), 1.69(2H, d) |
| 53 | 517 | in DMSO-d6: 10.6(1H, br. s), 7.25–7.50(12H, m), 6.88(2H, d), 5.22(1H, s), 4.46(1H, br. s), 4.01(2H, t), 3.54(2H, t), 3.20–3.40(2H, m), 2.90–3.20 (2H, m), 2.92(3H, br. s), 2.67(4H, s), 2.10–2.50(5H, m), 1.83(2H, quintet), 1.69(2H, d) |
| 51 | 531 | in DMSO-d6: 10.7(1H, br. s), 7.25–7.50(12H, m), 6.87(2H, d), 5.22(1H, br. s), 4.35(1H, br. s), 3.95(2H, t), 3.44(2H, t), 3.20–3.40(2H, m), 2.90–3.20 (2H, m), 2.93(3H, br. s), 2.68(4H, s), 2.00–2.50(5H, m), 1.65–1.80(4H, m), 1.50–1.60(2H, m) |
| 52 | 559 | in DMSO-d6: 10.5(1H, br. s), 7.25–7.50(12H, m), 6.87(2H, d), 5.21(1H, s), 4.26(1H, br. s), 3.93(2H, t), 3.38(2H, br. t), 3.20–3.40(2H, m), 2.90–3.20(2H, m), 2.93(3H, br. s), 2.67(4H, s), 2.10–2.40(5H, m), 1.60–1.80(4H, m), 1.30–1.50(6H, m) |
| 53 | 545 | in DMSO-d6: 10.6, 10.5(total 1H, each br. s), 7.30–7.60(11H, m), 7.16–7.24(1H, m), 6.97, 6.95(total 1H, each dd), 6.88, 6.83(total 1H, each d), 5.38, 5.22(total 1H, each br. s), 4.89, 4.85(total 2H, each s), 4.20, 4.14(total 2H, each q), 3.20–3.50(2H, m), 2.92(3H, br. s), 2.60–3.20(8H, m), 2.24(3H, br. s), 1.65, 1.40(total 2H, each d), 1.23, 1.18(total 3H, each t), |

TABLE 14

| Comp'd No. | Mass (FAB: (M + H)+) | 1H-NMR δ:ppm (measured in CDCl3 unless specifically indicated) |
|---|---|---|
| 54 | 573 | in DMSO-d6: 10.7, 10.4(total 1H, each br. s), 7.30–7.60 (11H, m), 7.18–7.26(1H, m), 6.95–7.02(1H, m), 6.92(1H, dd), 5.33, 5.16(total 1H each br. s), 4.00–4.20(4H, m), 3.20–3.40(2H, m), 2.95–3.15(2H, m), 2.93(3H, br. s), 2.68(4H, s), 2.50–2.75(2H, m), 2.40–2.50(2H, m), 2.25(3H, br. s), 2.07, 1.95(total 2H, each quintet), 1.70, 1.43(total 2H, each d), 1.20, 1.17(total 3H, each t) |
| 55 | 601 | in DMSO-d6: 10.8, 10.5(total 1H, each br. s), 7.30–7.60(11H, m), 7.18–7.24(1H, m), 6.98(1W d), 6.88–6.95(1H, m), 5.30, 5.10(total 1H, each br. s), 3.95–4.10(4H, m), 3.20–3.50(2H, m), 2.90–3.20(2H, m), 2.93(3H, br. s), 2.50–2.80(6H, m), 2.20–2.40 (2H, m), 2.24(3H, br. s), 1.30–1.90(8H, m), 1.18, 1.16(total 3H, each t) |
| 56 | 573 | in DMSO-d6: 9.80, 9.35(total 1H, each br. s), 7.30–7.70(11H, m), 7.10–7.20(1H, m), 6.94(1H, dd), 6.54, 6.50(total 1H, each dd), 5.35, 5.22(total 1H, each br. s), 4.15(2H, q), 3.20–3.50(2H, m), 3.00–3.20(2H, m), 2.94(3H, br. s), 2.60–2.75(6H, m), 2.25(3H, br. s), 1.72(2H, d), 1.66, 1.49(total 6H, each s), 1.12(3H, t) |
| 57 | 516 | in DMSO-d6: 10.42, 10.39(total 1H, each br. s), 7.57(1H, br. s), 7.30–7.50(11H, m), 7.30(1H, br s), 7.24(1H, ddd), 6.90–7.00(1H, m), 6.89, 6.84(total 1H, each d), 5.49, 5.46(total 1H, each s), |

TABLE 14-continued

| Comp'd No. | Mass (FAB: (M + H)+) | $^1$H-NMR δ:ppm (measured in CDCl$_3$ unless specifically indicated) |
|---|---|---|
| 58 | 545 | 4.55, 4.51(total 2H, each s), 3.20–3.40(2H, m), 2.70–3.20(5H, m), 2.68(4H, s), 2.61(2H, ddd), 2.25(3H, br. s), 1.87, 1.54(total 2H, each d) in DMSO-d$_6$: 10.7(1H, br. s), 7.30–7.50(10H, m), 7.25(1H, dd), 6.95–7.05(2H, m), 6.78(1H, dd), 5.35(1H, s), 4.73(2H, s), 4.16(2H, q), 3.20–3.40(2H, m), 2.90–3.10(2H, m), 2.92(3H, br. s), 2.68(4H, s), 2.37(2H, ddd), 2.25(3H, br. s), 1.69(2H, d), 1.20 (3H, t) |

TABLE 15

| Comp'd No. | Mass (FAB: (M + H)+) | $^1$H-NMR δ:ppm (measured in CDCl$_3$ unless specifically indicated) |
|---|---|---|
| 59 | 573 | in DMSO-d$_6$: 10.8(1H, br. s), 7.30–7.50(1H, m), 7.23(1H, dd), 6.90–7.10(2H, m), 6.79(1H, d), 5.33 (1H, s), 4.06(2H, q), 3.97(2H, t), 3.20–3.40(2H, m), 2.90–3.20(2H, m), 2.92(3H, br. s), 2.68(4H, s), 2.44(2H, t), 2.30–2.50(2H, m), 2.25(3H, br. s), 1.96(2H, quintet), 1.68(2H, d), 1.17(3H, t) |
| 60 | 601 | in DMSO-d$_6$: 10.8(1H, br. s), 7.30–7.50(10H, m), 7.23(1H, dd), 6.95–7.05(2H, m), 6.78(1H, dd), 5.32(1H, s), 4.04(2H, q), 3.93(2H, t), 3.20–3.40(2H, m), 2.90–3.10(2H, m), 2.92(3H, br. s), 2.68(4H, s), 2.39(2H, ddd), 2.29(2H, t), 2.00–2.40(3H, m), 1.60–1.80(4H, m), 1.58(2H, quintet), 1.40–1.50(2H, m), 1.17(3H, t) |
| 61 | 545 | in DMSO-d$_6$: 10.5(1H, br. s), 7.30–7.50(12H, m), 6.88(2H, d), 5.25(1H, s), 4.73(2H, s), 4.16(2H, q), 3.20–3.40(2H, m), 2.90–3.10(2H, m), 2.93(3H, br. s), 2.67(4H, s), 2.00–2.50(5H, m), 1.69(2H, d), 1.21 (3H, t) |
| 62 | 573 | in DMSO-d$_6$: 10.7(1H, br. s), 7.25–7.50(12H, m), 6.87(2H, d), 5.23(1H, br. s), 4.06(2H, q), 3.96(2H, t), 3.20–3.40(2H, m), 2.90–3.20(2H, m), 2.93(3H, br. s), 2.68(4H, s), 2.43(2H, t), 2.10–2.50(5H, m), 1.95(2H, quintet), 1.69(2H, d), 1.17(3H, t) |
| 63 | 601 | in DMSO-d$_6$: 10.6(1H, br. s), 7.25–7.50(12H, m), 6.87(2H, d), 5.22(1H, s), 4.04(2H, q), 3.92(2H, t), 3.20–3.40(2H, m), 2.90–3.20(2H, m), 2.93(3H, br. s), 2.68(4H, s), 2.10–2.50(5H, m), 2.29(2H, t), 1.60–1.80(4H, m), 1.58(2H, quintet), 1.35–1.50(2H, m), 1.17(3H, t) |

TABLE 16

| Comp'd No. | Mass (FAB: (M + H)+) | $^1$H-NMR δ:ppm (measured in CDCl$_3$ unless specifically indicated) |
|---|---|---|
| 64 | 487 | 7.20–7.50(10H, m) 7.10(1H, ddd) 7.04(1H, dd) 6.75–6.85(2H, m) 3.30 (2H, q) 2.82(2H, q) 2.65–2.75(2H, m) 2.35–2.55(4H, m) 2.00–2.20(4H, m) 1.92(2H, d) 1.13(3H, t) –0.01(3H, t) |
| 65 | 485 | 7.20–7.40(10H, m) 7.05–7.15(2H, m) 6.75–6.85 (2H, m) 3.36(2H, t) 2.70–2.90(2H, m) 2.40–2.60 (4H, m) 2.40(2H, t) 2.00–2.30(4H, m) 1.98 (2H, d) 1.56(2H, quintet) 1.46(2H, quintet) |
| 66 | 573 | 7.15–7.50(12H, m) 6.96(1H, dd) 6.75(1H, d) 4.65(2H, s) 4.50(1H, br) 4.27(2H, q) 3.36(2H, q) 2.84(2H, q) 1.80–3.00(12H, m) 1.30(3H, t) 1.19(3H, t) 0.01(3H, t) |
| 67 | 531 | 7.15–7.50(12H, m) 6.93(1H, dd) 6.87(1H, d) 5.00(1H, br) 4.00–4.10 (2H, m) 3.90–4.00(2H, m) 3.36(2H, q) |

TABLE 16-continued

| Comp'd No. | Mass (FAB: (M + H)+) | $^1$H-NMR δ:ppm (measured in CDCl$_3$ unless specifically indicated) |
|---|---|---|
|  |  | 2.55–3.00(7H, m) 2.40–2.55(2H, m) 2.25–2.35(2H, m) 1.95–2.05(2H, m) 1.59(2H, d) 1.18(3H, t) 0.00(3H, t) |
| 68 | 529 | 7.47(1H, dd) 7.25–7.40(10H, m) 7.20(1H, ddd) 6.93 (1H, ddd) 6.87(1H, dd) 4.80(1H, br) 4.06(2H, t) 3.97 (2H, t) 3.58(2H, t) 2.40–2.80 (9H, m) 2.30–2.40 (2H, m) 2.05–2.15(2H, m) 1.67(2H, quintet) 1.62(2H, d) 1.52(2H, quintet) |
| 69 | 571 | 7.20–7.50(11H, m) 7.19(1H, ddd) 6.96(1H, dd) 6.75 (1H, d) 4.65(2H, s) 4.38(1H, s) 4.27(2H, q) 3.59(2H, t) 2.60–2.80(2H, m) 2.40–2.60 (6H, m) 1.95–2.40(6H, m) 1.67(2H, quintet) 1.52(2H, quintet) 1.29(3H, t) |
| 70 | 517 | in DMSO-d6: 7.30–7.50(11H, m) 7.10(1H, ddd) 6.86 (1H, dd) 6.77(1H, d) 4.33(2H, s) 2.00–3.10(16H, m) 1.56(2H, d) |
| 71 | 543 | in DMSO-d6: 7.30–7.50(11H, m) 7.09(1H, dd) 6.86 (1H, dd) 6.77(1H, d) 4.34(2H, s) 3.40–3.60(2H, m) 3.00–3.20(2H, m) 2.75–2.95(2H, m) 2.50–2.70(6H, m) 2.30–2.50(2H, m), 1.40–1.70(6H, m) |
| 72 | 475 | 7.39(1H, dd) 7.20–7.35(10H, m) 7.20(1H, dd) 6.93 (1H, t) 6.86(1H, d) 6.03(1H, br) 4.05(2H, t), 3.92(2H, t), 3.70(1H, br) 2.80–2.95(2H, m), 2.73(2H, t), 2.63 (2H, t), 2.40–2.57(4H, m), 1.82(2H, d), |

TABLE 17

| | | |
|---|---|---|
| 73 | 531 | 6.97(1H, t) 6.88(1H, d) 7.10–7.40(12H, m) 4.86(1H, br) 4.45 (2H, t) 4.25(1H, s) 4.21(2H, t) 3.98(1H, t) 3.15(2H, q) 2.70–2.85(2H, m) 2.50–2.65(2H, m) 2.30–2.50(4H, m) 2.00–2.20 (4H, m) 1.45(2H, q) 1.31(2H, q) 0.89(3H, t) |
| 74 | 573 | in DMSO-d6: 10.5, 10.4(total 1H, each br. s) 7.30–7.60(11H, m) 7.15–7.25(1H, m) 6.90–7.00(1H, m) 6.87, 6.83(total 1H, each d) 5.35, 5.21(total 1H, each br. s) 4.88, 4.78(total 2H, each 4.20, 4.14(total 2H, each q) 3.10–3.40(4H, m) 2.50–3.10 (10H, m) 1.65, 1.39(total 2H, each d) 1.23, 1.18(total 3H, each t) 1.13(3H, br. t) –0.04(3H, br. t) |
| 75 | 531 | in DMSO-d6: 10.4, 10.2(total 1H, each br. s) 7.30–7.60(11H, m) 7.18–7.26(1H, m) 6.88–7.02(2H, m) 4.80–5.40(2H, br.) 4.03, 3.97(total 2H, each t) 3.78, 3.64(total 2H, each t) 2.95–3.45(6H, m) 2.55–2.90(8H, m) 1.61, 1.43(total 2H, each d) 1.05–1.24(3H, br. t) –0.25 ~ 0.10(3H, br. t) |
| 76 | 529 | in DMSO-d6: 10.4, 10.2(total 1H, each br. s) 7.30–7.60(11H, m) 7.22(1H, ddd) 6.97(1H, d) 6.93(1H, dd) 5.31, 5.27(total 1H, each s) 5.10, 4.75(total 1H, each br. s) 4.02, 3.98(total 2H, each t) 3.75–3.85, 3.60–3.70(total 2H, each m) 3.40–3.55 (2H, m) 3.20–3.35(2H, m) 3.00–3.15(2H, m) 2.55–3.00 (6H, m) 2.30–2.40(2H, m) 1.40–1.70(6H, m) |
| 77 | 571 | in DMSO-d6: 10.5, 10.4(total 1H, each br. s) 7.20–7.60(12H, m) 6.92–7.00(1H, m) 6.88, 6.84(total 1H, each dd) 5.36, 5.23 (total 1H, each br. s) 4.89, 4.85(total 2H, each s) 4.19, 4.15 (total 2H, each q) 3.15–3.55(4H, m) 2.95–3.15(2H, m) 2.60–2.90(6H, m) 2.25–2.45(2H, m) 1.35–1.75(6H, m) 1.22, 1.19 (total 3H, each t) |
| 78 | 517 | in DMSO-d6: 13.0(1H, br.) 10.6, 10, 4(total 1H, each br. s) 7.30–7.60(11H, m) 7.20(1H, ddd) 6.94(1H, dd) 6.83(1H, d) 5.30(1H, br.) 4.79, 4.74(total 2H, each s) 2.50–3.50(13H, m) 2.25(3H, br. s) 1.67, 1.41(total 2H, each d) |
| 79 | 543 | 10.8(1H, br. s) 7.10–7.50(12H, m) 6.95(1H, dd) 6.78(1H, d) 5.50(2H, br) 4.61(2H, s) 3.56(2H, t) 3.30–3.40(2H, m) 3.15–3.30(2H, m) 2.75–2.90(4H, m) 2.55–2.75(2H, m) 2.40(2H, t) 2.20(2H, d) 1.71(2H, quintet) 1.55(2H, quintet) |

TABLE 18

| 80 | 475 | 11.27(1H, br) 7.45(1H, dd) 6.92(1H, t) 6.87(1H, d) 6.01(1H, s) 5.80(1H, s) 4.00–4.06(4H, m) 3.79(1H, br) 3.30–3.40(2H, m) 3.10–3.30(2H, m) 2.90–3.10(6H, m) 1.75–1.90(2H, m) |
| --- | --- | --- |
| 81 | 531 | 12.11(1H, br) 7.20–7.35(12H, m) 6.97(1H, t) 6.86(1H, d) 4.85(1H, br) 4.57(1H, s) 4.40–4.50(2H, m) 4.15–4.25(2H, m) 3.97(1H, t) 3.25–3.45(4H, m) 3.10–3.20(2H, m) 2.85–2.95(2H, m) 2.65–2.80(4H, m) 2.15–2.27(2H, m) 1.37–1.50(2H, m) 1.20–1.37 (2H, m) 0.89(3H, t) |

Test 1: Action on the ileum sample excised from a guinea pig

A Hartley male guinea pig of about 500 g in weight was employed. From its ileocecum, 15 to 30 cm of the ileum was excised and a longitudinal muscle sample attached with the Auerbach's plexus was prepared. Using the resulting sample, opioid receptor activity of a test drug was measured in accordance with the method proposed by Oka, et al (Eur. J. Pharmacol., 77; 137–141, 1982). The agonist activity was indicated in terms of relative potency to DAMGO ([D-Ala$^2$, N-MePhe$^4$, Gly$^5$-ol]-enkephalin), a selective $\mu$-opioid agonist. The test drug was confirmed to be an opioid agonist by antagonism by naloxone.

Results are shown in Table 19.

TABLE 19

| Compound No. | Relative potency |
| --- | --- |
| 39 | 10 |
| 41 | 8.4 |
| 42 | 8.0 |
| 43 | 5.0 |
| 53 | 8.3 |
| 57 | 6.0 |
| 77 | 8.2 |
| 78 | 26 |
| DAMGO | 1.0 |
| Morphine | 0.14 |
| Loperamide | 4.3 |

Test 2: Action against righting reflex of a 10-day-old rat

It has been revealed (Oka, et al., Dev. Brain Res. 69; 271–276, 1992) that the righting reflex of a 10-day-old rat is suppressed by a $\mu$-opioid receptor agonist and this suppression is antagonized by naloxone. The test drug was therefore administered subcutaneously to a 10-day-old rat to study the administration amount required for disappearance of righting reflex.

Results are shown in Table 20.

TABLE 20

| Comp'd No. | Administration amount required for disappearance of righting reflex ($\mu$mol/kg) |
| --- | --- |
| 38 | 1 |
| 42 | 1 |
| 53 | 0.3 |
| morphine | 3 |

Capability of Exploitation in Industry

The 4-hydroxy-4-phenylpiperidine derivative or salt thereof (1) according to the present invention exhibits excellent $\mu$-opioid agonist action and is therefore useful as a peripheral analgesic.

What is claimed is:

1. A 4-hydroxy-4-phenylpiperidine compound represented by the following formula (1):

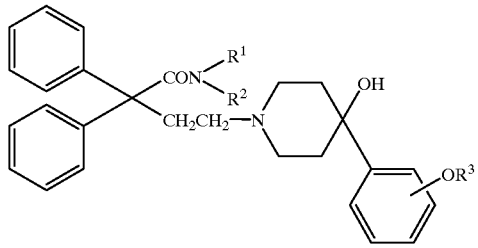

wherein, $R^1$ and $R^2$ are the same or different and each independently represents a hydrogen atom, a lower alkyl group or a cycloalkyl group, or $R^1$ and $R^2$ may form a heterocyclic ring together with the adjacent nitrogen atom, $R^3$ represents a hydrogen atom or a group —$(CR^4R^5)_n$—Y, in which, $R^4$ and $R^5$ each represents a hydrogen atom or a lower alkyl group, Y represents a group —COOR$^6$, —CONR$^7$R$^8$, —OR$^9$ or —OCOR$^{10}$, in which R$^6$, R$^9$ and R$^{10}$ each independently represents a hydrogen atom, a lower alkyl group or a cycloalkyl group, $R^7$ and $R^8$ are the same or different and each independently represents a hydrogen atom, a lower alkyl group or a cycloalkyl group or $R^7$ and $R^8$ may form a heterocyclic ring together with the adjacent nitrogen atom, and n stands for 1 to 6, or salt thereof.

2. The compound according to claim 1, wherein $R^1$ and $R^2$ are the same or different and each independently represents a hydrogen atom, a $C_{1-6}$ alkyl group or a $C_{3-8}$ cycloalkyl group, or $R^1$ and $R^2$ may form, together with the adjacent nitrogen atom, a 3- to 8-membered heterocyclic ring, $R^3$ represents a hydrogen atom or a group —$(CR^4R^5)_n$—Y, in which, $R^4$ and $R^5$ each represents a hydrogen atom or a $C_{1-6}$ alkyl group, Y represents a group —COOR$^6$, —CONR$^7$R$^8$, —OR$^9$ or —OCOR$^{10}$, in which R$^6$, R$^9$ and R$^{10}$ each independently represents a hydrogen atom, a $C_{1-6}$ alkyl group or a $C_{3-8}$ cycloalkyl group, $R^7$ and $R^8$ are the same or different and each independently represents a hydrogen atom, a $C_{1-6}$ alkyl group or a $C_{3-8}$ cycloalkyl group or $R^7$ and $R^8$ may form, together with the adjacent nitrogen atom, a 3- to 8-membered heterocyclic ring.

3. A pharmaceutical composition, comprising:

a 4-hydroxy-4-phenylpiperidine compound or salt thereof as claimed in claim 1 and a pharmaceutically acceptable carrier.

4. A method for treating pain, comprising:

administering to a subject in need thereof a 4-hydroxy-4-phenylpiperidine compound or salt thereof as claimed in claim 1.

5. The pharmaceutical composition according to claim 3 which is a peripheral analgesic.

6. The method according to claim 4, wherein said compound is administered per day in an amount of about 0.005 to 2 mg per kg of said subject.

* * * * *